United States Patent [19]
Kim et al.

[11] Patent Number: 6,130,336
[45] Date of Patent: Oct. 10, 2000

[54] PROCESS FOR PREPARING PACLITAXEL

[75] Inventors: Kyoung Soo Kim; Ki Byung Chai, both of Seoul; Young Ho Moon, Sungnam; Kwang Ok Lee, Seoul; Nam Du Kim, Yongin; Tae Hee Ha, Sungnam; Jung Ae Shin, Seoul; Gwan Sun Lee, Seoul; Wan Joo Kim, Seoul, all of Rep. of Korea

[73] Assignee: Hanmi Pharm., Co. Ltd., Rep. of Korea

[21] Appl. No.: 09/242,736

[22] PCT Filed: Aug. 25, 1997

[86] PCT No.: PCT/KR97/00157

§ 371 Date: Feb. 23, 1999

§ 102(e) Date: Feb. 23, 1999

[87] PCT Pub. No.: WO98/08832

PCT Pub. Date: Mar. 5, 1998

[30]    Foreign Application Priority Data

Aug. 27, 1996 [KR]   Rep. of Korea ............... 96/35754

[51] Int. Cl.[7] ............... C07D 263/02; C07D 305/00
[52] U.S. Cl. ............................ 548/215; 549/510
[58] Field of Search ............... 548/215; 549/510

[56]    References Cited

U.S. PATENT DOCUMENTS

| | | |
|---|---|---|
| 5,635,531 | 6/1997 | Chen . |
| 5,948,919 | 9/1999 | Sisti et al. ............... 549/510 |
| 6,043,375 | 3/2000 | Bourzat et al. ............... 548/215 |
| 6,057,452 | 5/2000 | Wuts et al. ............... 548/215 |

FOREIGN PATENT DOCUMENTS

| | | |
|---|---|---|
| 0 735 036 A1 | 10/1996 | European Pat. Off. . |
| WO 94/22856 | 10/1994 | WIPO . |
| WO 96/40666 | 12/1996 | WIPO . |
| WO 96/40667 | 12/1996 | WIPO . |
| WO 97/15562 | 5/1997 | WIPO . |

OTHER PUBLICATIONS

Joydeep Kant, et al., Synthesis and Antitumor Properties of Novel 14–β–Hydroxytaxol and Related Analogues, Bioorganic & Medicinal Chemistry Letters, vol. 4, No. 13, pp. 1565–1570, 1994.

Iwao Ojima, et al., Synthesis and Biological Activity of 14–Hydroxydocetaxel, Bioorganic & Medicinal Chemistry Letters, vol. 4, No. 13, pp. 1571–1576, 1994.

Jean–Pierre Pulicani, et al., Electrochemical Reduction of Taxoids: Selective Preparation of 9–dihydro– , 10–deoxy– and 10–deacetoxy–Taxoids, Tetrahedron Letters, vol. 35, No. 28, pp. 4999–5002, 1994.

Gunda I. Georg, et al., Stereoselective Synthesis of 9β–Hydroxytaxanes via Reduction with Samarium Diiodide, Tetrahedron Letters, vol. 36, No. 11, pp. 1783–1786, 1995.

R. M. Straubinger, et al., Pharmacology and Antitumor Effect of Novel Paclitaxel Formulations, Taxane Anticancer Agents, ©1995 American Chemical Society, Chapter 8, pp. 110–121.

*Primary Examiner*—Deborah C. Lambkin
*Attorney, Agent, or Firm*—Hunton & Williams

[57]    ABSTRACT

The present invention elates to a process for preparing paclitaxel represented by formula (1) characterized in that: (a) an oxazolidine derivative represented by formula (2) or its salt in which X represents halogen, is coupled with a 7-trihaloacetyl-baccatin III represented by formula (3) in which $R_1$ represents trihaloacetyl, in a solvent in the presence of a condensing agent to produce an oxazolidine substituent-containing taxane represented by formula (4) in which X and $R_1$ are each as previously defined; (b) the oxazolidine ring is opened in a solvent in the presence of an acid, and the product thus obtained is reacted with benzoyl chloride in the presence of a base to produce a protected paclitaxel wherein the hydroxy group at 7-position is protected with trihaloacetyl group represented by formula (5) in which $R_1$ is as previously defined; (c) then the protecting group at 7-position is removed by ammonia or a salt of ammonia with a weak acid in a solvent.

30 Claims, No Drawings

PROCESS FOR PREPARING PACLITAXEL

TECHNICAL FIELD

The present invention relates to a novel process for preparing paclitaxel represented by the following formula (I):

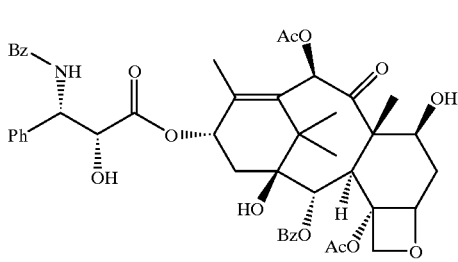

(1)

in which

Ph represents phenyl,

Ac represents acetyl,

Bz represents benzoyl, and hereinafter they have the same meaning.

The present invention also relates to novel intermediates which may be used in the process for preparing paclitaxel of formula 1; and to processes for preparing them.

BACKGROUND ART

Paclitaxel of formula1, a terpene taxane derivative, is a potent anti-tumor chemotherapeutics having a broad spectrum of anti-leukemia and anti-tumor activity. Accordingly, many concerns have been focused on this compound in both area of biology and chemistry. Paclitaxel has also been allowed to be commercially marketed as an anti-tumor agent against ovarian cancer and breast cancer in several countries including the United States.

Hitherto, paclitaxel has been provided by separation from the bark of *Taxus brevifolia* which is a kind of western yew tree. However, since the separation and purification procedures are very burdensome and further only small amount of paclitaxel is contained in the bark of that evergreen tree, the amount of paclitaxel thus provided can hardly meet the more and more increasing commercial need.

Recently, the chemists have extensively studied about semi-syntheses which are applicable for preparing paclitaxel and about new synthetic methods for the same compound including processes for preparing the intermediates. However, a lot of synthetic methods reported heretofore have not shown a satisfactory result.

For example, WO 93/06094 discloses a process for preparing paclitaxel by reacting a beta-lactam compound and 7-triethylsilyl-baccatin III, then by deprotecting, as depicted in the following reaction scheme 1. Now, this is recognized as the shortest procedure to obtain the desired paclitaxel compound.

Reaction Scheme 1

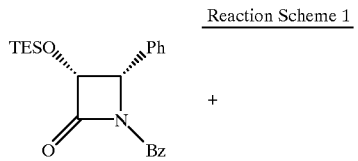

+

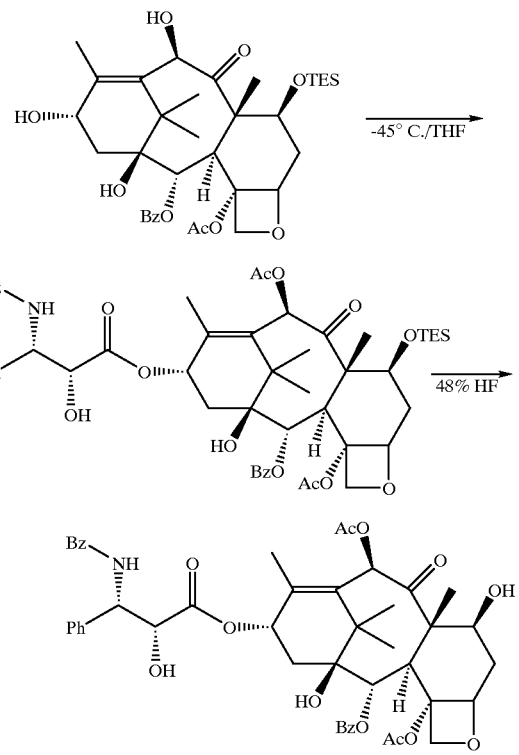

in which

TES represents triethylsilyl, and hereinafter has the same meaning.

Although this method has a merit that the coupling reaction can be readily carried out by using the beta-lactam compound, it also has many disadvantages such that the synthesis of the beta-lactam compound itself is very difficult, the coupling reaction should be proceeded at a low temperature of −45° C. under an anhydrous condition, a toxic acid having a strong corrosive action against glass products as well as properties hard to treat (i.e.,48% HF) should be used during the process for removing the triethylsilyl (TES) group used as a protecting group for a taxane derivative, etc.

In addition, as depicted in the following reaction scheme 2, a process wherein an oxazolidine compound instead of the beta-lactam is coupled with a 7-Troc-baccatin III in the presence of dicyclohexylcarbodiimide or 2-dipyridylcarbonate is described in Commercon et al., Tetrahedron Letters, pp5185–5188, 1992.

Reaction Scheme 2

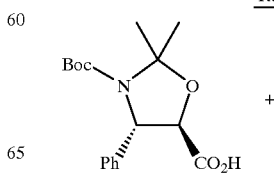

+

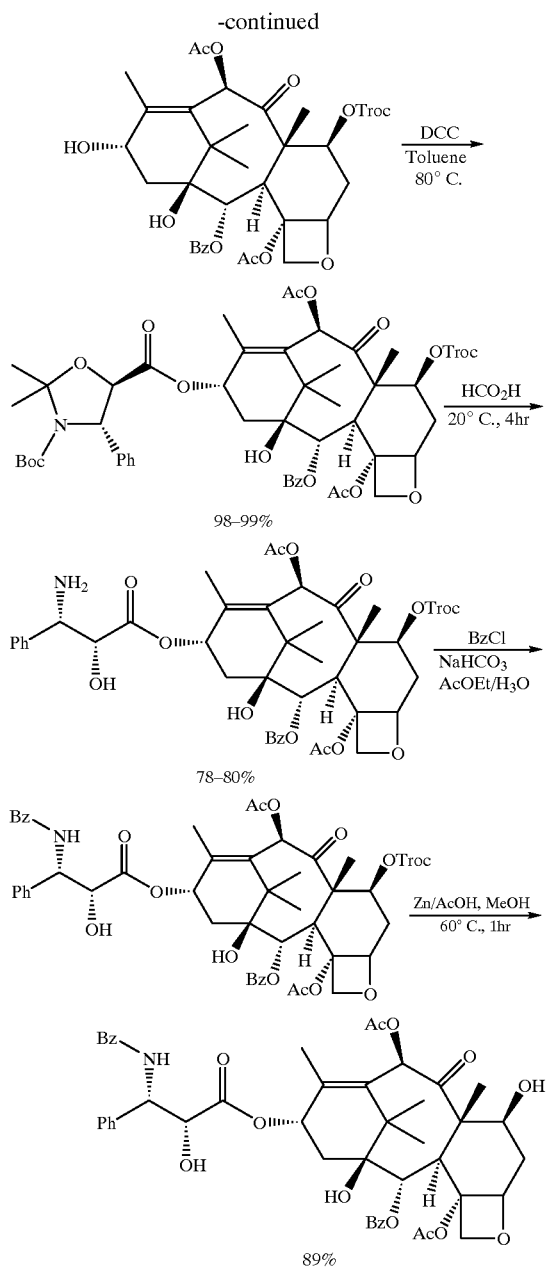

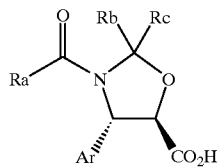

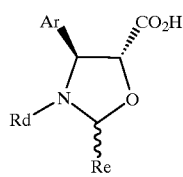

in which

Boc represents t-butoxycarbonyl,

Troc represents trichloroethoxycarbonyl, and hereinafter they have the same meaning.

In the above process for preparing paclitaxel, a new protecting group for the taxane derivative (-Troc) which is different from that used in the prior process of reaction scheme 1 (-TES) has been used. However, according to the use of this novel protecting group, more reaction steps should be carried out to obtain the desired product, vigorous reaction conditions are required for the protection as well as deprotection reaction, and as a result the total yield becomes low. Therefore, the process of reaction scheme 2 is understood inferior to that of reaction scheme 1.

In the process of reaction scheme 2, an oxazolidine derivative is coupled with a taxane derivative to prepare paclitaxel. As the known oxazolidine derivatives which have been used for such a purpose, a compound represented by the following formula 6 (see, WO 94/10169) and a compound represented by the following formula 7 (see, Korean Patent Appln. No. 95-703548) can be mentioned.

in which $R_a$ represents phenyl or $R_fO$, wherein $R_f$ represents alkyl, alkenyl, alkynyl, cycloalkyl, cycloalkenyl, phenyl or heterocyclic compound containing nitrogen atom, $R_b$ and $R_c$ independently of one another represent hydrogen, alkyl, phenylalkyl, phenyl, alkoxyphenyl or dialkoxyphenyl, or $R_b$ and $R_c$ can form a cyclic chain having 4 to 7 ring atoms.

in which $R_d$ represents hydrogen, benzoyl or $R_gOCO-$, wherein $R_g$ represents alkyl, alkenyl, cycloalkyl, cycloalkenyl or bicycloalkyl, $R_e$ represents trihalomethyl or phenyl substituted by trihalomethyl.

The oxazolidine derivative of formula 6 above has various substituents at 2-position of the ring and the amine group at 3-position is necessarily protected by a substituted carbonyl group. It is because the amine group at 3-position is apt to react with the carboxylic acid at 5-position of another oxazolidine molecule if it is not protected. This kind of side reaction has greater reactivity than the coupling reaction between the oxazolidine derivative and the taxane derivative, and as a result the coupling reaction cannot be carried out favorably. Another case can be seen from the oxazolidine derivative of formula 7. That is, in case the substituent at 2-position of the oxazolidine ring is trihalomethyl or phenyl substituted by trihalomethyl, the desired coupling reaction can be carried out without any side reaction such as self coupling between oxazolidine molecules although the amine group at 3-position is not protected. If no protection for the amine group at 3-position of oxazolidine ring is required, several advantages including no need for removing the protecting group at a later step may be anticipated.

While, another process for preparing paclitaxel, as depicted in the following reaction scheme 3, is disclosed in Korean Patent Appln. No. 94-702930.

Reaction Scheme 3

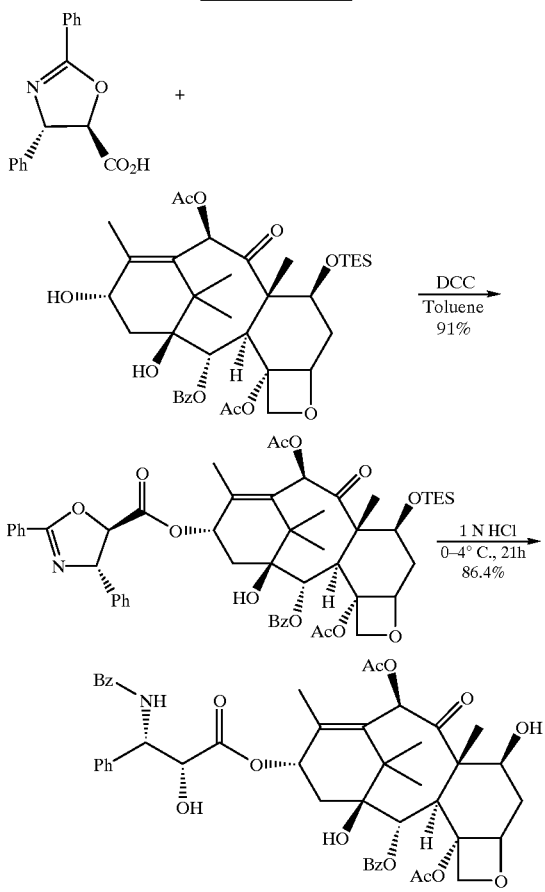

In the above process, paclitaxel is prepared by coupling an oxazoline derivative with a taxane derivative having a hydroxy group directly attached to C-13 to produce a taxane derivative having an oxazoline substituent, opening the oxazoline ring, then deprotecting. When such an oxazoline derivative substituted by a phenyl group at 2-position and a taxane derivative protected with triethylsilyl group are used as starting materials, however, opening reaction of the oxazoline ring and deprotection reaction may not readily performed. That is, severe reaction conditions such as strong acidity and long reaction time (i.e., 1N-HCl (5.5 eq.), 0° C., 21 hrs) are required, nevertheless, productivity and reaction yield are still low.

As aforementioned, the earlier developed processes for preparing paclitaxel use various side chain substituents such as beta-lactam derivative, oxazolidine derivative, or oxazoline derivative. But, all those substituents have some problems, for example, synthesis of itself or coupling with a taxane derivative is difficult, opening the substituent ring requires severe conditions, etc.

Another important point that should be considered is the choice of the protecting group for taxane derivative. As the protecting groups for taxane derivative reported up to the present, triethylsilyl and trichloro-ethoxycarbonyl can be mentioned. In order to remove such protecting groups, extremely acidic conditions or extended reaction time such as reacting for 14 hours in the presence of 48HF/pyridine; reacting for 4 hours in formic acid solvent; reacting at a condition of zinc, AcOH/MeOH=1/1 and 60° C.; reacting for 30 hours in 0.5% HCl/EtOH; etc. are usually required.

Moreover, those protecting groups have the following problems. In the case of triethylsilyl group, an excessive amount (20 eq.) of the expensive triethylsilyl chloride should be used in the protection reaction (see, WO 93/06094); and in the case of trichloroethoxycarbonyl group, complicated synthetic pathway should be applied for preparing the protected taxane derivative since this protecting group has no selectivity (see, Commercon, et al., Tetrahedron Letters, pp5185–5188, 1992).

DISCLOSURE OF INVENTION

Thus, the present inventors have extensively studied for years to develop a more improved process for preparing paclitaxel by solving the various problems of prior art processes as mentioned above. As a result, we have identified that the opening reaction of the side chain substituent and deprotection reaction can be easily performed under very mild conditions if coupling is carried out between a novel oxazolidine derivative wherein two halomethyl substituents are present at 2-position and the amine at 3-position is not protected and a novel taxane derivative wherein the hydroxy group at 7-position is protected by trihaloacetyl. Particularly, the present inventors have found a surprising fact that if the novel oxazolidine derivative having two halomethyl substituents at 2-position is used, the coupling reaction of the oxazolidine derivative with the taxane derivative may well be carried out without any side reaction such as self coupling between oxazolidine molecules although the amine at 3-position is not protected.

Therefore, it is an object of the present invention to provide a novel process for preparing paclitaxel represented by the following formula 1

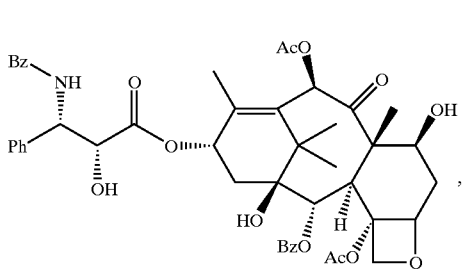

(1)

characterized in that (a) an oxazolidine derivative represented by the following formula 2 or its salt:

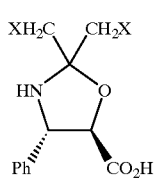

(2)

in which X represents halogen, is coupled with a 7-trihaloacetyl-baccatin III represented by the following formula 3:

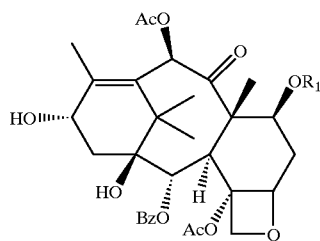

(3)

in which R₁ represents trihaloacetyl, in a solvent in the presence of a condensing agent to produce an oxazolidine substituent-containing taxane represented by the following formula 4:

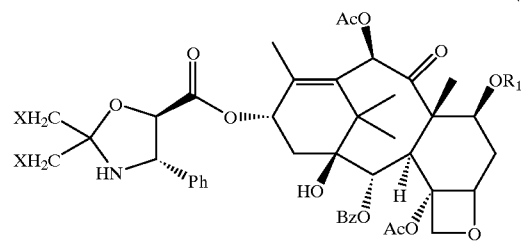

(4)

in which X and R₁ are each as previously described; (b) the oxazolidinie ring is opened in a solvent in the presence of an acid, and the product thus obtained is reacted with benzoyl chloride in the presence of a base to produce a protected paclitaxel wherein the hydroxy group at 7-position is protected with trihaloacetyl group represented by the following formula 5:

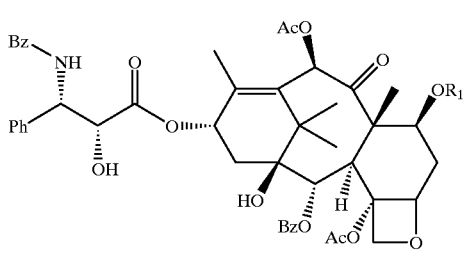

(5)

in which R₁ is as previously described; (c) then the protecting group at 7-position is removed by ammonia or a salt of ammonia with a weak acid in a solvent.

It is another object of the present invention to provide novel starting materials oxazolidine derivative of formula 2 and taxane derivative of formula 3, and processes for preparing them.

BEST MODE FOR CARRYING OUT THE INVENTION

The process for preparing paclitaxel according to the present invention can be summarized as the following reaction scheme 4

Reaction Scheme 4

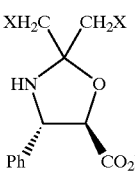

(2)

+

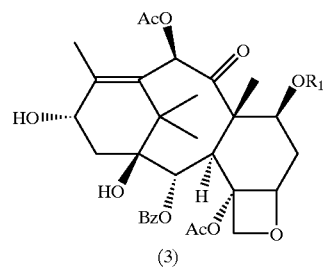

(3)

Step (a)

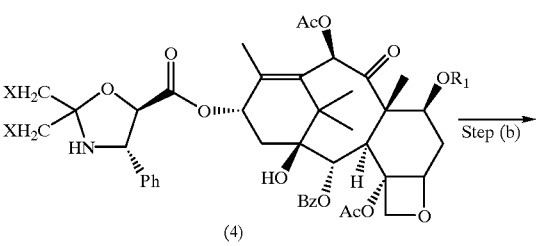

(4)

Step (b)

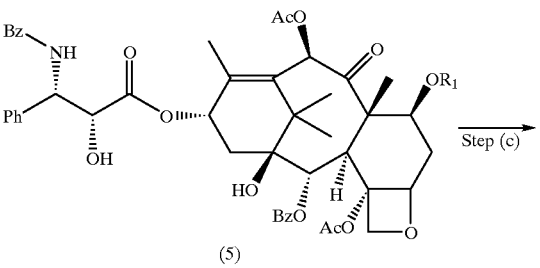

(5)

Step (c)

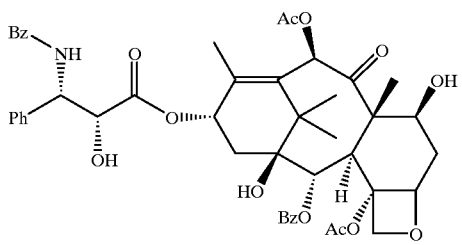

(1)

in which X and R are each as previously described.

The process described in the above reaction scheme 4 will be more specifically explained below.

The step (a) reaction for producing the oxazolidine substituent-containing taxane of formula 4 by coupling the 7-trihaloacetyl-baccatin III of formula 3 with the oxazolidine derivative of formula 2 is preferably carried out at temperatures ranging from 20 to 60° C. Solvents suitable for this reaction include ethers such as tetrahydrofuran, diisopropylether, methyl t-butylether or dioxane; ketones such as methyl isobutyl ketone; nitriles such as acetonitrile; esters such as ethylacetate, isopropylacetate or n-butylacetate; aliphatic hydrocarbons such as pentane, hexane or heptane; chlorinated hydrocarbons such as dichloromethane, chloroform or 1,2-dichloroethane; aromatic hydrocarbons such as benzene, toluene or xylene; amides such as dimethylacetamide or dimethylformamide.

In the coupling reaction, the oxazolidine derivative of formula 2 is used in an excessive amount, for example, an equimolar amount to 3 times molar amount, preferably 1.5 to 3 times molar amount, with respect to the compound of formula 3. This coupling reaction is carried out in the presence of a condensing agent, and optionally in the presence of an activating agent. As the condensing agent, carbodiimides such as dicyclohexylcarbodiimide, and reactive carbonates such as 2-dipyridylcarbonate can be mentioned. And as the activating agent, dialkylaminopyridines such as 4-dimethylaminopyridine, 4-pyrrolidinopyridine and the like can be mentioned. Generally, the condensing agent is used in a stoichiometric amount with respect to the oxazolidine compound of formula 2, and the activating agent is used in a stoichiometric amount or less with respect to the 7-trihaloacetyl-baccatin III of formula 3.

The step (b) reaction for preparing the compound of formula 5 comprises opening the oxazolidine ring and reacting the opened product with benzoyl chloride in the presence of a base. This reaction merely requires a weak acidic condition wherein 1 to 1.5 equivalents of acid with respect to the compound of formula 4 is used, which is an effect resulted from the use of the novel oxazolidine derivative of formula 2 as a starting material. Acids which can be used for adjusting the acidity of the reaction solution include hydrochloric acid, sulfuric acid, formic acid, nitric acid, acetic acid, trifluoroacetic acid, p-toluenesulfonic acid, methanesulfonic acid and benzoic acid. The acid can be used in a stoichiometric amount with respect to the compound of formula 4, however, 1.5 equivalents of acid is preferably used in order to complete the reaction within the shortest time and to minimize the side reactions. As the solvent, one or more selected from a group consisting of ethers such as tetrahydrofuran, diethylether or dioxane; nitriles such as acetonitrile, ketones such as acetone or methyl isobutyl ketone, esters such as ethylacetate, isopropylacetate or n-butylacetate; chlorinated hydrocarbons such as dichloromethane, chloroform or 1,2-dichloroethane; aromatic hydrocarbons such as benzene, toluene or xylene; and amides such as dimethylacetamide or dimethylformamide can be used. This reaction is preferably carried out at temperatures ranging from −20 to 60° C. for 10 to 30 minutes.

The reaction solution thus obtained is neutralized with a suitable base, diluted with water and then reacted with benzoylchloride to produce the paclitaxel protected with trihaloacetyl at 7-position of formula 5. The reactant benzoylchloride is used in a stoichiometric amount, more specifically 1 to 1.2 equivalents, with respect to the oxazolidine substituent-containing taxane of formula 4. As the base, one or more water-soluble bases selected from a group consisting of sodium bicarbonate, potassium bicarbonate, sodium carbonate, potassium carbonate, sodium hydroxide, potassium hydroxide and lithium hydroxide may be used in an excessive amount, preferably 3 to 20 equivalents, with respect to the compound of formula 4.

Finally, in step (c), the trihaloacetyl group at 7-position of the compound 5 is removed by using ammonia or a salt of ammonia with a weak acid to prepare the desired compound paclitaxel of formula 1. In this reaction, aqueous ammonia or ammonia-organic solvent solution having a concentration of 5 to 40% may be used in a stoichiometric amount or more, preferably 1 to 5 equivalents, with respect to the compound of formula 5. When a salt of ammonia with a weak acid replaces ammonia, it is used in an amount of 1 to 5 equivalents with respect to the compound of formula 5. The weak acid can be formic acid, acetic acid or propionic acid.

As the solvent, one or more selected from a group consisting of alcohols such as methanol, ethanol or isopropyl alcohol; ethers such as tetrahydrofuran, diethylether or dioxane; nitriles such as acetonitrile; esters such as ethylacetate, isopropylacetate or n-butylacetate; chlorinated hydrocarbons such as dichloromethane, chloroform or 1,2-dichloroethane; aromatic hydrocarbons such as benzene, toluene or xylene; and amides such as dimethylacetamide or dimethylformamide can be used. This reaction is preferably carried out at temperatures ranging from 0 to 60° C. Hitherto, very strong acidic conditions have generally been required to eliminate the protecting group at 7-position of taxane. However, the present invention makes it possible to readily remove the protecting group under weak alkali or almost neutral conditions wherein ammonia or a salt of ammonia with a weak acid is used.

The 7-trihaloacetyl-baccatin III of formula 3 used as a starting material in the process for preparing paclitaxel is itself a novel compound, therefore it is another object of the present invention to provide the novel taxane derivative of formula 3.

The 7-trihaloacetyl-baccatin III of formula 3 can be prepared by (d) reacting a 10-deacetyl-baccatin III represented by the following formula 8:

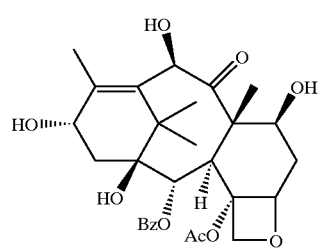

(8)

with trihaloacetyl halide in a solvent in the presence of a base to provide a 10-deacetyl-7-trihaloacetyl-baccatin III represented by the following formula 9:

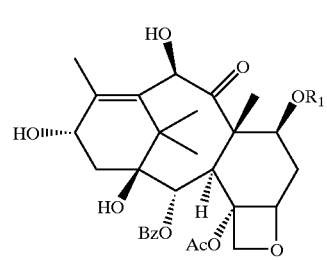

(9)

in which $R_1$ represents trihaloacetyl, then (e) reacting the compound of formula 9 thus obtained with acetyl halide in a solvent in the presence of a base.

The process for preparing the compound of formula 3 can be summarized as the following reaction scheme 5.

Reaction Scheme 5

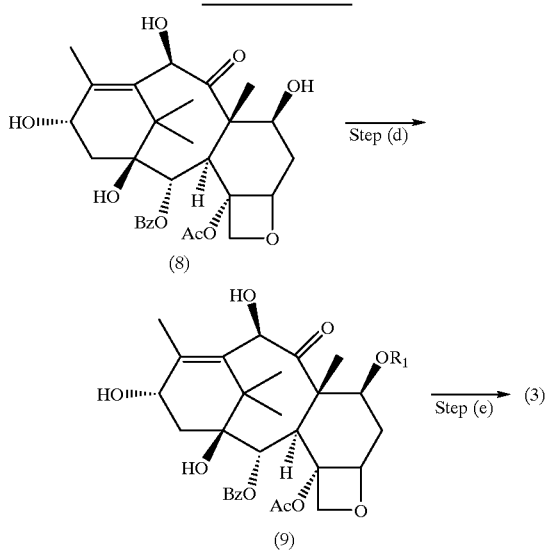

in which $R_1$ is as previously described.

In step (d) of the reaction scheme 5, the hydroxy group at 7-position of the 1 0-deacetyl-baccatin III of formula 8 is protected by trihaloacetyl to provide the 10-deacetyl-7-trihaloacetyl-baccatin III of formula 9. In the earlier processes using triethylsilyl or trichloroethoxycarbonyl as a protecting group, about 20 times molar excess of triethylsilyl should be used or some annoying procedure consisting of several steps should be carried out. In contrast, this step according to the present invention use only a stoichiometric amount of trihaloacetyl to selectively protect the hydroxy group at 7-position of the taxane derivative. One selected from a group consisting of trichloroacetyl chloride, trichloroacetyl bromide, tribromoacetyl chloride, tribromoacetyl bromide, trifluoroacetyl chloride, trifluoroacetyl bromide, triiodoacetyl chloride and triiodoacetyl bromide can be used as the trihaloacetyl halide, and it is usually used in a stoichiometric amount or more, preferably 1 to 1.5 equivalents, with respect to the compound of formula 8. Solvents which can be suitably used for this reaction include ethers such as tetrahydrofuran, diisopropylether, methyl t-butylether or dioxane; ketones such as methyl isobutyl ketone; nitrites such as acetonitrile; esters such as ethylacetate, isopropylacetate or n-butylacetate; aliphatic hydrocarbons such as pentane, hexane or heptane; chlorinated hydrocarbons such as dichloromethane, chloroform or 1,2-dichloroethane; aromatic hydrocarbons such as benzene, toluene or xylene; amides such as dimethylacetamide or dimethylformamide; and basic solvents such as pyridine. When pyridine is used as the solvent, the reaction can be performed without a base. As the appropriate base, pyridine, triethylamine, imidazole, DBU, diisopropylethylamine, potassium t-butoxide, sodium ethoxide, n-butyllithium, phenyllithium, lithium diisopropylamide, sodium hydride or lithium bistrimethylsilylamide can be mentioned This reaction is preferably carried out at temperatures ranging from −20 to 60° C.

In step (e), the novel 7-trihaloacetyl-baccatin III of formula 3 is prepared by reacting the 1-deacetyl-7-trihaloacetyl-baccatin III of formula 9 with acetyl halide in a solvent in the presence of a base. The acetyl halide is used in a stoichiometric amount or more, preferably 1 to 8 equivalents, with respect to the 10-deacetyl-7-trihaloacetyl-baccatin III of formula 9. Solvents and bases which can be suitably used, and reaction temperature range are the same as mentioned for step (d).

An oxazolidine derivative represented by the following formula 2a is itself a novel compound, therefore it is yet another object of the present invention.

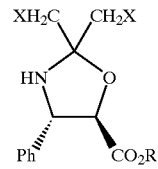

(2a)

in which

X is as previously described, and

R represents hydrogen or $C_1$–$C_3$alkyl.

The most important feature of this compound is that two halomethyl substituents are present at 2-position of the oxazolidine ring and the amine at 3-position is not protected. In addition, this compound includes the compound of formula 2 which is the starting material of the process for preparing paclitaxel according to the present invention.

The oxazolidine derivative of formula 2a as defined above can be prepared by reacting a (2R,3S)-phenylisoserine derivative represented by the following formula 10:

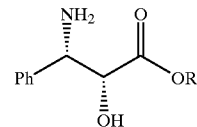

(10)

in which R is as previously described, with a compound represented by the following formula 11:

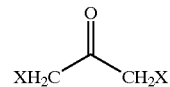

(11)

in which X is as previously described, in a solvent in the presence of an acid catalyst.

The compound of formula 2a which is prepared after carrying out the above process includes two types of compounds, one is a free acid form (R=hydrogen) and the other is an ester form (R=alkyl). Therefore, if the free acid form is desirable, hydrolysis may be further carried out on the ester form compound of formula 2a.

All the earlier processes for preparing the oxazolidine derivative have used only the phenylisoserine alkylester (ester form) as the starting material.

However, in the present invention, the oxazolidine derivative can be prepared from phenylisoserine as well as phenylisoserine alkylester. That is, the present inventors have found an astonishing fact that the novel oxazolidine derivative of formula 2 (R=hydrogen) can be directly prepared from phenylisoserine. In case phenylisoserine, not ester form, is used as the starting material, two steps (one step for preparing phenylisoserine methylester from phenylisoserine and the other step for removing the methylester group from the oxazolidine derivative) can be saved, therefore it is another advantage resulted from the present invention.

The process for preparing the oxazolidine derivative of formula 2a can be depicted as the following reaction scheme 6:

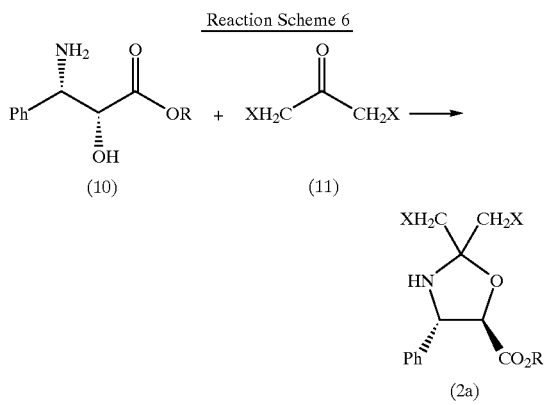

Reaction Scheme 6 in which X and R are each as previously described.

The oxazolidine derivative of formula 2a wherein R is hydrogen or alkyl is prepared by reacting the (2R,3S)-phenylisoserine derivative with the halogenated acetone of formula 11 in a solvent in the presence of an acid catalyst. As the acid catalyst p-toluenesulfonic acid, methanesulfonic acid, trifluoromethylsulfonic acid, pyridinium p-toluenesulfonate, amberlite IR-120, etc. can be used, and as the solvent one or more selected from a group consisting of ethers such as tetrahydrofuran, diisopropylether, methyl t-butylether or dioxane; nitriles such as acetonitrile; esters such as ethylacetate, isopropylacetate or n-butylacetate; chlorinated hydrocarbons such as dichloromethane, chloroform or 1,2-dichloroethane; aromatic hydrocarbons such as benzene, toluene or xylene; and amides such as dimethylacetamide or dimethylformamide can be used. When the (2R,3S)-phenylisoserine (R=hydrogen), which is hard to solve in solvent used, is used as the starting material, a good yield may be obtained by adding a small quantity of amides into the reaction solution, and also the curtailment of reaction time can be accomplished by adding the amides in an amount of 1/20 times or more with respect to the total volume of solvent. This reaction is preferably carried out at temperatures ranging from 30 to 100° C.

When the compound of formula 2a wherein R is alkyl is obtained, it can be further hydrolyzed to the compound of formula 2a wherein R is hydrogen. Water-soluble bases such as hydroxides can be used as the hydrolyzing agent. The hydroxides which can be used for this purpose include alkali metal hydroxides such as, for example, lithium hydroxide, sodium hydroxide, potassium hydroxide, etc. The hydrolyzing agent is preferably used in an amount of 1 to 2 equivalents with respect to the oxazolidine compound of formula 2a wherein R is alkyl. As the reaction solvent, a solvent mixture of water-miscible organic solvent and water in a ratio of 10:1 to 100:1 by volume can be used. Water-miscible organic solvents which can be suitably used herein include methanol, ethanol, isopropyl alcohol, tetrahydrofuran, dimethylformamide, dimethylacetamide, acetone and acetonitrile. This reaction is preferably carried out at temperatures ranging from −20 to 60° C. After the hydrolysis is completed, the organic solvent is removed by distillation under reduced pressure to obtain the oxazolidine compound of formula 2a wherein R is hydrogen in the form of an inorganic salt ($RCO_2M$). In order to convert the salt form into a free acid form ($RCO_2H$), an acid or buffer solution having pH 5 to 7 is used. Acids which can be used for this purpose include hydrochloric acid, formic acid, acetic acid and trifluoroacetic acid. The acid is used in the same equivalent to the alkali metal hydroxide used in the hydrolysis.

Since the ring opening reaction after coupling may be readily carried out under mild conditions when the compound of formula 2a is used, this compound according to the present invention is more advantageous than the existing 2-phenyl-2-oxazoline derivative which requires a very strong acidic condition and long reaction time (that is, 1N-HCl (5.5 eq.), 0° C., 21 hrs) during the ring opening and deprotection reaction.

The (2R,3S)-phenylisoserine derivative or its salt which are used as a starting material in the reaction of scheme 6 can be obtained by a process known in the art (see, U.S. Pat. No. 5,420,337; Commercon et al., Tetrahedron Letters, 33, pp5185–5188, 1992; and Kim et al., Korean Patent Appln. No. 96-7304).

Since the oxazolidine compound of formula 2 (R=hydrogen) thus obtained is unstable in the presence of an acid, it is desirable to store the compound in a salt form with a tertiary amine base as represented by the following formula 2b:

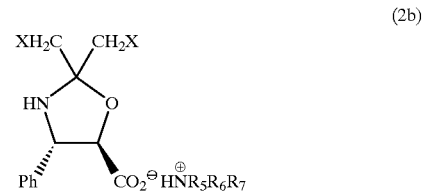

(2b)

in which

X is as previously described, $R_5$, $R_6$ and $R_7$ independently of one another represent $C_1$–$C_4$alkyl or phenylalkyl, or $R_5$ and $R_6$ together can form a cyclic chain having 4 to 7 ring atoms The present invention will be more specifically explained by the following examples. However, it should be understood that the examples are intended to illustrate but not to in any manner limit the scope of the present invention.

EXAMPLE 1

Synthesis of 10-deacetyl-7-trichloroacetyl-baccatin III 30 g (0.055 mol) of 10-Deacetyl-baccatin III was dissolved in 1.35 l of chloroform, 134 ml (30 eq.) of pyridine was added dropwise thereto. and then the reaction mixture was stirred for 10 minutes. After 12 g (0.066 mol) of trichloroacetyl chloride was slowly added, the resulting mixture was stirred at room temperature for 30 minutes. Then, 3 g (0.017 mol) of trichloroacetyl chloride was further added thereto and the whole mixture was stirred for 20 minutes. The solvent was removed under reduced pressure, 100 ml of water was added to the residue, and then the resulting solution was extracted with 700 ml of ethylacetate. The organic layer thus obtained was washed with aqueous sodium chloride solution, dried over anhydrous magnesium sulfate, and then distilled under reduced pressure. The residue was dissolved in 200 ml of toluene and then cooled down to 0° C. The resulting fine solid was filtered and then washed with 200 ml of hexane to obtain 36 g (Yield 95% ) of the pure title compound.

M.P.: 216° C.; $[a]_D^{25}$=−45.3° (c=1, $CHCl_3$); $^1$H NMR (300 MHz,$CDCl_3$): δ 8.12(d,J=7.3 Hz,2H), 7.67–7.49(m, 3H), 5.67(d,J=6.9 Hz,1H), 5.61–5.55(m,1H), 5.35(s,1H), 5.00(d,J=8.6 Hz,1H), 4.90(m,1H), 4.38(d,J=8.5 Hz,1H), 4.22(d,J=8.4Hz,1H), 3.99(m,1H), 2.77–2.71(m,1H), 2.32–1.09(m,18H).

EXAMPLE 2

Synthesis of 7-trichloroacetyl-baccatin III 36 g (0.052 mol) of 10-deacetyl-7-trichloroacetyl-baccatin III prepared in Example 1 was dissolved in 1.25 l of chloroform. 125 ml (30 eq.) of pyridine was added dropwise thereto and the mixture was stirred for 10 minutes. To the mixture was slowly added 38 g (0.309 mol) of acetyl bromide, then the resulting mixture was stirred at room temperature for 3 hours. The solvent was removed under reduced pressure, 100 ml of water was added to the residue, and then the resulting solution was extracted with 700 ml of ethylacetate. The organic layer thus obtained was washed with aqueous sodium chloride solution, dried over anhydrous magnesium sulfate, and then distilled under reduced pressure. The residue was dissolved in 200 ml of toluene and then cooled down to 0° C. The resulting fine solid was filtered and then washed with 200 ml of hexane to obtain 35.9 g (Yield 94%) of the pure title compound.

M.P.: 180° C.; $[a]_D^{25}$=−62.3 (c=1, $CHCl_3$); $^1$H NMR(300 MHz,$CDCl_3$): δ 8.13(d,J=7.3 Hz,2H), 7.67–7.49(m,3H), 6.50 (s,1H), 5.76–5.67(m,2H), 5.00(d,J=8.8 Hz,1H), 4.89 (m,1H), 4.37(d,J=9.0 Hz,1H), 4.19 (d,J=9.4 Hz,1H), 4.06 (m,2H), 2,73–2.69(m,1H), 2.34–1.11(m,21H).

EXAMPLE 3

Synthesis of (4S;5R)-2,2'-di(chloromethyl)-4-phenyl- 1,3-oxazolidine-5-carboxylic acid methylester 10.0 g (0.051 mol) of (2R,3S)-phenylisoserine methylester, 6.51 g (0.051 mol) of 1,3-dichloroacetone and 0.1 g of pyridinium p-toluenesulfonate were dissolved in 100 ml of acetonitrile. The mixture was stirred at 80° C. for 40 minutes and then the reaction solvent was removed by distillation under reduced pressure. 100 ml of water was added to the residue, which was then extracted with 200 ml of ethylacetate. The moisture contained in the organic layer was eliminated over anhydrous magnesium sulfate and then the solvent was distilled off under reduced pressure to obtain 14.1 g (Yield 90%) of the title compound.

$^1$H NMR (300 MHz,$CDCl_3$): δ 7.47–7.28 (m,5 H), 4.64–4.53(m,2 H), 3.95(s,2 H), 3.84(d,J=6.0 Hz,2 H), 3.78 (s,3 H), 3.10(d,J=10.2 Hz,1 H).

EXAMPLE 4

Synthesis of (4S,5R)-2,2'-di(chloromethyl)-4-phenyl-1,3-oxazolidine-5-carboxylic acid triethylamine salt (Method I)

After 13.0 g (0.043 mol) of (4S,5R)-2;2'-di(chloromethyl)-4-phenyl- 1,3-oxazolidine-5-carboxylic acid methylester prepared in Example 3 was dissolved in 50 ml of methanol, 15.7 ml (0.047 mol) of 3.0N aqueous lithium hydroxide solution was added dropwise thereto. The reaction mixture was stirred at normal temperature for 30 minutes and then reaction solvent was removed by distillation under reduced pressure. 30 ml of water and 15.7 ml (0.047 mol) of 3.0N aqueous hydrochloric acid solution were added to the residue, which was then extracted with 200 mg of ethylacetate. The moisture contained in the organic layer was eliminated over anhydrous magnesium sulfate and then 9.0 ml (0.065 mol) of triethylamine was added dropwise thereto. The solvent was distilled off under reduced pressure to obtain 15.7 g (Yield 94%) of the title compound.

$^1$ H NMR (300 MHz,$CDCl_3$): δ 7.52–7.28 (m,5 H), 4.57(d,J=7.6 Hz,1 H), 4.46(d,J=7.6 Hz,1 H), 3.94–3.81(m,4 H), 3.07(q,J=7.1 Hz,6 H), 1.28(t,J=7.1 Hz,9 H).

EXAMPLE 5

Synthesis of (4S,5R)-2,2'-di(chloromethyl)-4-phenyl- 1,3-oxazolidine-5-carboxylic acid triethylamine salt (Method II)

10.0 g (0.055 mol) of (2R,3S)-phenylisoserine, 7.0 g (0.055 mol) of 1,3-dichloroacetone, 5 ml of dimethylformamide, and 0.1 g of pyridinium p-toluenesulfonate were dissolved in 100 ml of acetonitrile. The mixture was stirred at 80° C. for one hour and then the reaction solvent was removed by distillation under reduced pressure. 100 ml of water was added to the residue, which was then extracted with 200 ml of ethylacetate. The moisture contained in the organic layer was eliminated over anhydrous magnesium sulfate and then 11.5 ml (0.083 mol) of triethylamine was added dropwise thereto. The solvent was distilled off under reduced pressure to obtain 19 g (Yield 88%) of the title compound.

EXAMPLE 6

Synthesis of 13-[(4S,5R)-2,2'-di(chloromethyl)-4-phenyl-1,3-oxazolidinyl-carbonyl ]-baccatin III 15.7 g (0.040 mol) of (4S,5R)-2,2'-di(chloromethyl)-4-phenyl-1,3-oxazolidine-5-carboxylic acid triethylamine salt prepared in Example 4 or 5 and 9.8 g (0.013 mol) of 7-trichloroacetyl-baccatin III prepared in Example 2 were dissolved in 120 ml of toluene together with 8.2 g (0.040 mol) of dicyclohexylcarbodiimide and 0.1 g of 4-dimethylaminopyridine. The resulting mixture was stirred at normal temperature for one hour, filtered through a cellite pad, and then distilled under reduced pressure to remove the reaction solvent. The residue was subjected to column chromatography (eluent: ethylacetate/hexane=1/2, v/v) to obtain 12.6 g (Yield 94.5%) of the title compound as a pale yellow solid.

M.P.: 187° C.; $[a]_D^{25}$ =−24.8° (c=0.44, $CHCl_3$); $^1$ H NMR(300 MHz,$CDCl_3$): δ 8.03(d,J=7.2 Hz,2 H), 7.68–7.45 (m,8 H), 6.39 (s,1 H), 6.26 (t,J=8.5 Hz,1 H),5.76–5.69(m,2 H), 5.67–5.62(m,2 H), 4.89 (d,J=8.4 Hz,1 H), 4.65(m,1 H), 4.43(d,J=8.2 Hz,1 H), 4.27(d,J=8.4 Hz,1 H), 4.11(d,J=7.3 Hz,1 H), 4.04(s,2 H), 3.90(m,1 H), 3.82(d,J=9.8 Hz,2 H), 3.20(d,J=10.5 Hz), 2.65(m,1 H), 2.15–1.14(m,21 H).

EXAMPLE 7

Synthesis of Paclitaxel 12 g (0.012 mol) of the coupling product prepared in Example 6 was dissolved in 50 ml of ethylacetate. 1.5 ml (0.018 mol) of conc. hydrochloric acid was added dropwise thereto and the mixture was stirred at normal temperature for 20 minutes. The reaction solution was neutralized with 12 g (0.14 mol) of sodium bicarbonate. 100 ml of water was added to the mixture and then 1.7 ml (0.014 mol) of benzoyl chloride was added dropwise thereto. The reaction solution was stirred at normal temperature for 10 minutes, extracted with 300 ml of ethylacetate, and then dried over anhydrous magnesium sulfate. The solvent was removed by distillation under reduced pressure and the resulting residue was dissolved in 50 ml of a solvent mixture of methanol and tetrahydrofuran (3/1, v/v). 2.0 M Ammonia (6.0 ml, 0.012 mol) dissolved in methanol was added dropwise thereto, the resulting mixture was stirred at normal temperature for one hour, and then the reaction solvent was distilled off under reduced pressure. The residue was subjected to column chromatography (eluent: ethylacetate/hexane=2/1, v/v) to obtain 9.39 g (Yield 92%) of the title compound as a white solid.

[1] H NMR(300 MHz,CDCl$_3$): δ 8.15(d,J=7.2 Hz,2 H), 7.76(d,J=7.2 Hz,2 H), 7.64–7.37(m,11 H), 7.04(d,J=8.8 Hz,1 H), 6.29(s,1 H), 6.25(dd,J=8.9 Hz, J=8.9 Hz,1 H), 5.80(dd,J1=2.5 Hz,J2=8.7 Hz,1 H), 5.69(d,J=7.1 Hz, 1 H), 4.95(dd,J 1=2.3 Hz,J2=10 Hz,1 H), 4.81(dd,J 1=2.5 Hz,J2= 5.0 Hz, 1 H), (m,1 H), 4.32(d,J=8.5 Hz,1 H), 4.22(d, J=8.5 Hz,1 H), 3.83(d,J=6.9 Hz,1 H), 3.66(d,J=5.3 Hz,1 H), 2,54–1.16(m,22 H).

The advantages resulted from the present invention can be summarized as follows.

The existing processes for preparing paclitaxel generally use triethylsilyl or trichloroethoxycarbonyl group for the protection of the hydroxy group at 7-position of baccatin III. The removal of these protecting groups requires very vigorous condition using strong acid. In the present invention, however, the hydroxy group at the same position is protected by trihaloacetyl group which can be easily removed under weak alkali or almost neutral mild conditions (for example, 1 equivalent of ammonia/organic solvent, 20° C., 1 hr; or 1.2 equivalent of ammonium acetate/organic solvent, 20° C., 3 hrs). Therefore, according to the present invention, paclitaxel can be prepared with facility and more economically. Particularly, the mildness of reaction condition is expected to be a conspicuous advantage when the process is applied on an industrial scale.

Another advantage of this invention lies in the use of the novel oxazolidine derivative wherein two halomethyl substituents are present at 2-position and the amine at 3-position is not protected as a substituent for baccatin III. This novel oxazolidine derivative does not cause side reactions such as self coupling and makes the ring opening reaction after coupling easy, and thus increases the productivity. Moreover, since this novel oxazolidine derivative can be directly prepared from phenylisoserine, the curtailment of operation can be accomplished.

Consequently, by using the appropriate protecting groups which are easy to remove, the present process may be conveniently carried out under mild conditions with a high total yield.

What is claimed is:

1. A process for preparing paclitaxel represented by the following formula 1:

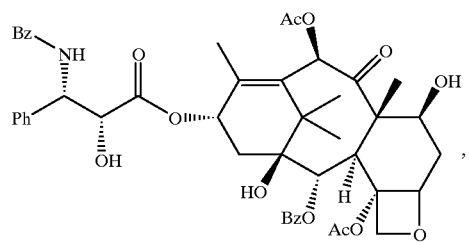

characterized in that (a) an oxazolidine derivative represented by the following formula 2 or its salt:

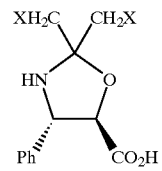

in which X represents halogen, is coupled with a 7-trihaloacetyl-baccatin III represented by the following formula 3:

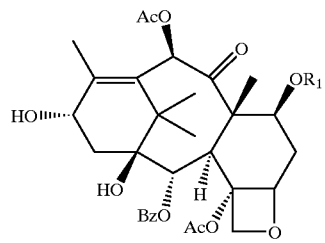

in which $R_1$ represents trihaloacetyl, in a solvent in the presence of a condensing agent to produce an oxazolidine substituent-containing taxane represented by the following formula 4:

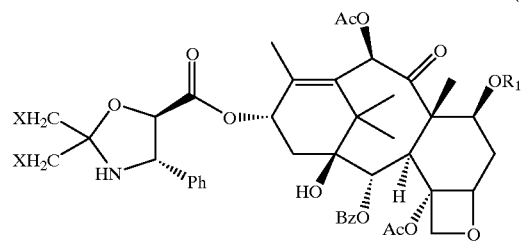

in which X and $R_1$ are each as previously defined; (b) the oxazolidine ring is opened in a solvent in the presence of an acid, and the product thus obtained is reacted with benzoyl chloride in the presence of a base to produce a protected paclitaxel wherein the hydroxy group at 7-position is protected with trihaloacetyl group represented by the following formula 5:

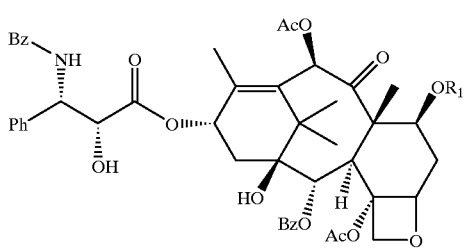 (5)

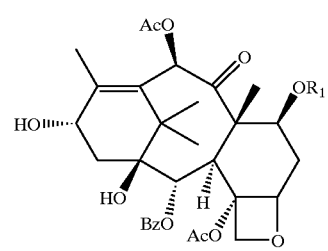 (3)

in which $R_1$ is as previously defined; (c) then the protecting group at 7-position is removed by ammonia or a salt of ammonia with a weak acid in a solvent.

2. The process of claim 1, wherein X is chloro and $R_1$ is trichloroacetyl.

3. The process of claim 1, wherein the solvent of step (a) is one or more selected from a group consisting of tetrahydrofuran, diisopropylether, methyl t-butylether, dioxane, methyl isobutyl ketone, acetonitrile, ethylacetate, isopropylacetate, n-butylacetate, pentane, hexane, heptane, dichloromethane, chloroform, 1,2-dichloroethane, benzene, toluene, xylene, dimethylacetamide and dimethylformamide.

4. The process of claim 1, wherein the condensing agent of step (a) is carbodiimides or reactive carbonates.

5. The process of claim 1, wherein the reaction of step (a) is carried out in the presence of 4-dimethylaminopyridine or 4-pyrrolidinopyridine as an activating agent.

6. The process of claim 1, wherein the solvent of step (b) is one or more selected from a group consisting of tetrahydrofuran, diethylether, dioxane, acetonitrile, acetone, methyl isobutyl ketone, ethylacetate, isopropyl acetate, n-butylacetate, dichloromethane, chloroform, 1,2-dichloroethane, benzene, toluene, xylene, dimethylacetamide and dimethylformamide.

7. The process of claim 1, wherein in step (b) the acid selected from a group consisting of hydrochloric acid, sulfuric acid, formic acid, nitric acid, acetic acid, trifluoroacetic acid, p-toluenesulfonic acid, methanesulfonic acid and benzoic acid is used in an amount of 1.5 equivalents with respect to the oxazolidine substituent-containing taxane of formula 4.

8. The process of claim 1, wherein in step (b) the benzoyl chloride is used in an amount of 1 to 1.2 equivalents with respect to the oxazolidine substituent-containing taxane of formula 4.

9. The process of claim 1, wherein the base of step (b) is one or more selected from a group consisting of sodium bicarbonate, potassium bicarbonate, sodium carbonate, potassium carbonate, sodium hydroxide, potassium hydroxide and lithium hydroxide.

10. The process of claim 1, wherein in step (c) aqueous ammonia or ammonia-organic solvent solution having a concentration of 5 to 40% is used in an amount of 1 to 5 equivalents with respect to the compound of formula 5.

11. The process of claim 1, wherein in step (c) the salt of ammonia with a weak acid selected from a group consisting of formic acid, acetic acid and propionic acid is used in an amount of 1 to 5 equivalents with respect to the compound of formula 5.

12. A taxane derivative represented by the following formula 3:

in which $R_1$ represents trihaloacetyl.

13. The compound of claim 12, wherein $R_1$ is trichloroacetyl.

14. A process for preparing the taxane derivative of formula 3 as defined in claim 12 characterized in that (d) a 10-deacetyl-baccatin III represented by the following formula 8;

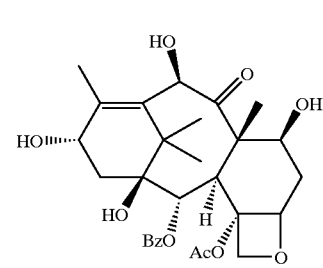 (8)

is reacted with trihaloacetyl halide in a solvent in the presence of a base to provide a 10-deacetyl-7-trihaloacetyl-baccatin III represented by the following formula 9:

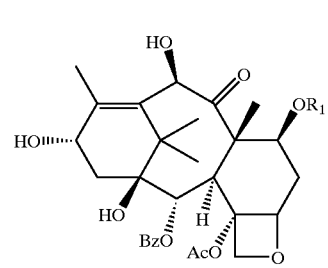 (9)

in which $R_1$ represents trihaloacetyl, then (e) the compound of formula 9 thus obtained is reacted with acetyl halide in a solvent in the presence of a base.

15. The process of claim 14, wherein in step (d) the trihaloacetyl halide selected from a group consisting of trichloroacetyl chloride, trichloroacetyl bromide, tribromoacetyl chloride, tribromoacetyl bromide, trifluoroacetyl chloride, trifluoroacetyl bromide, triiodoacetyl chloride and triiodoacetyl bromide is used in an amount of 1 to 1.5 equivalents with respect to the compound of formula 8.

16. The process of claim 14 or 15, wherein the trihaloacetyl halide is trichloroacetyl chloride.

17. The process of claim 14, wherein in step (e) the acetyl halide is used in an amount of 1 to 8 equivalents with respect to the compound of formula 9.

18. The process of claim 14 or 17, wherein the acetyl halide is acetyl bromide.

19. The process of claim 14, wherein in step (d) or (e) the solvent is one or more selected from a group consisting of tetrahydrofuran, diisopropylether, methyl t-butylether, dioxane, methyl isobutyl ketone, acetonitrile, ethylacetate, isopropylacetate, n-butylacetate, pentane, hexane, heptane, dichloromethane, chloroform, 1,2-dichloroethane, benzene, toluene, xylene, dimethylacetamide, dimethylformamide and pyridine.

20. The process of claim 14, wherein in step (d) or (e) the base is one or more selected from a group consisting of pyridine, triethylamine, imidazole, DBU, diisopropylethylamine, potassium t-butoxide, sodium ethoxide, n-butyllithium, phenyllithium, lithium diisopropylamide, sodium hydride and lithium bistrimethylsilylamide.

21. An oxazolidine derivative represented by the following formula 2a or its salt:

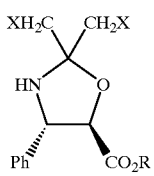

(2a)

in which

X is as defined in claim 1, and

R represents hydrogen or $C_1$–$C_3$alkyl.

22. The compound of claim 21, wherein it is the salt form represented by the following formula 2b:

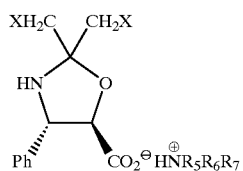

(2b)

in which

X is as defined in claim 1, $R_5$, $R_6$ and $R_7$ independently of one another represent $C_1$–$C_4$alkyl or phenylalkyl, or $R_5$ and $R_6$ together can form a cyclic chain having 4 to 7 ring atoms.

23. The compound of claim 21 or 22, wherein X is chloro.

24. A process for preparing the oxazolidine derivative as defined in claim 21 or its salt characterized in that a (2R,3S)-phenylisoserine derivative represented by the following formula 10:

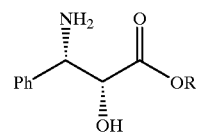

(10)

in which R is as defined in claim 21, is reacted with a compound represented by the following formula 11:

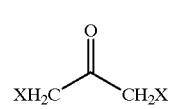

(11)

in which X is as defined in claim 1, in a solvent in the presence of an acid catalyst.

25. The process of claim 24, wherein the solvent is one or more selected from a group consisting of tetrahydrofuran, diisopropylether, methyl t-butylether, dioxane, acetonitrile, ethylacetate, isopropylacetate, n-butylacetate, dichloromethane, chloroform, 1,2-dichloroethane, benzene, toluene, xylene, dimethylacetamide and dimethylformamide.

26. The process of claim 24, wherein the acid catalyst is one or more selected from a group consisting of p-toluenesulfonic acid, methanesulfonic acid, trifluoromethylsulfonic acid, pyridinium p-toluenesulfonate and amberlite IR-120.

27. The process of claim 24, wherein the compound of formula 2a in which R is alkyl is further hydrolyzed in a solvent in the presence of a water-soluble base to obtain the compound of formula 2a in which R is hydrogen.

28. The process of claim 27, wherein the solvent is a mixture of water-miscible organic solvent and water in a ratio of 10:1 to 100:1 by volume.

29. The process of claim 28, wherein the water-miscible organic solvent is one or more selected from a group consisting of methanol, ethanol, isopropyl alcohol, tetrahydrofuran, dimethylformamide, dimethylacetamide, acetone and acetonitrile.

30. The process of claim 27, wherein the water-soluble base selected from a group consisting of lithium hydroxide, sodium hydroxide and potassium hydroxide is used in an amount of 1 to 2 equivalents with respect to the compound of formula 2a in which R is $C_1$–$C_3$alkyl.

* * * * *